US00PP13450P2

(12) United States Plant Patent
Olesen et al.

(10) Patent No.: US PP13,450 P2
(45) Date of Patent: Jan. 7, 2003

(54) SHRUB ROSE VARIETY 'POULERRY'

(76) Inventors: L. Pernille Olesen, Hillerødevejen 49, DK-3480, Fredensborg (DK); Mogens N. Olesen, Hillerødevejen 49, DK-3480, Fredensborg (DK)

( * ) Notice: Subject to any disclaimer, the term of this patent is extended or adjusted under 35 U.S.C. 154(b) by 77 days.

(21) Appl. No.: 09/676,602

(22) Filed: Sep. 27, 2000

(51) Int. Cl.[7] ..... A01H 5/00

(52) U.S. Cl. ..... Plt./108

(58) Field of Search ..... Plt./108, 102, 141, Plt./150

(56) References Cited

PUBLICATIONS

UPOV–ROM GTITM Computer Database 2001/06, GTI Jouve Retrieval Software, Citation for Rosa 'Poulerry'.*

Community Plant Variety Office. "Certificate on the Grant of Community Plant Variety Rights" Jun. 19, 2000. 6 pages. EU.

* cited by examiner

*Primary Examiner*—Bruce R. Campell
*Assistant Examiner*—June Hwu

(57) ABSTRACT

A new shrub rose plant which has abundant, red-purple flowers and attractive foliage. The variety successfully propagates from softwood cuttings and is suitable for year round production in commercial nurseries. This new and distinct variety has shown to be uniform and stable in the resulting generations from asexual propagation.

1 Drawing Sheet

CLASSIFICATION

Botanical: *Rosa hybrida.*

Commercial: Shrub.

SUMMARY OF THE INVENTION

The present invention constitutes a new and distinct variety of shrub rose plant which originated from a controlled crossing between 'POULor' and an unnamed seedling. The two parents were crossed, and the resulting seeds were planted in a controlled environment. The new variety is named 'POULerry'.

The new rose may be distinguished from its seed parent, 'POULor' (U.S. Plant Pat. No. 12,511), by the following combination of characteristics:

1. The bloom color of 'POULerry' is a more intensely reddish pink than 'POULor'.

2. The petal count of 'POULerry' is somewhat higher than that of 'POULor'.

3. The bloom size of 'POULerry' is larger than that of 'POULor'.

The new rose may be distinguished from its pollen parent, an unnamed seedling, by the following combination of characteristics:

1. The bloom coloration of 'POULerry' is a more intense pink than that of the pollen parent.

The objective of the hybridization of this rose variety for commercial greenhouse culture was to create a new and distinct variety with unique qualities, such as:

1. Uniform and abundant reddish-pink flowers that are semi-double and cup shaped;

2. Strong even growth with a free branching habit;

3. Flowers with a wild rose scent.

4. Glossy and disease resistant foliage which requires limited maintenance, making it ideal for use in landscapes.

The combination of qualities of this variety represents significant improvement over previously available commercial cultivars of this type and distinguishes 'POULerry' from all other varieties of which we are aware.

As part of their rose development program, L. Pernille Olesen and Mogens N. Olesen germinated the seeds from the aforementioned hybridization and conducted evaluations on the resulting seedlings in a controlled environment in Fredensborg, Denmark.

'POULerry' was selected by the inventors as a single plant from the progeny of the hybridization in Fredensborg, Denmark in May of 1993.

Asexual reproduction of 'POULerry' by cuttings and traditional budding was first done by L. Pernille and Mogens N. Olesen in their nursery in Fredensborg, Denmark in August, 1993. This initial and other subsequent propagations conducted in controlled environments have demonstrated that the characteristics of 'POULerry' are true to type and are transmitted from one generation to the next.

BRIEF DESCRIPTION OF THE DRAWING

The accompanying color illustration shows as true as is reasonably possible to obtain in color photographs of this type, the typical characteristics of the buds, flowers, leaves, stems, and a plant of 'POULerry'. Specifically illustrated in SHEET 1:

1. Stem showing the branches, leaves, buds and peduncles;

2. Flower bud, partially opened bud, and open bloom;

3. Flower petals, detached;

4. Sepals, receptacle, and pedicel;

5. A bare stem exhibiting thorns; and

6. Leaves.

DETAILED DESCRIPTION OF THE VARIETY

The following is a description of 'POULerry', as observed in its growth in a nursery in Jackson County, Oreg., on plants aged one year. Color references are made using The Royal Horticultural Society (London, England) Colour Chart, 1995, except where common terms of color are used.

For a comparison, several physical characteristics of the rose variety 'POULrijk', a shrub rose variety from the same inventors described and illustrated in U.S. Plant Pat. No. 12,519 issued Apr. 2, 2002, are compared to 'POULerry' in Chart 1.

CHART 1

| | 'POULerry' | 'POULrijk' |
|---|---|---|
| Petal Color | Upper Surface: Red Group 53C. Lower Surface: Red Group 53C to Red-Purple Group 57A. | Upper Surface: Red-Purple Group 58 C and D. Lower Surface: Red Group 53C to Red-Purple Group 57D. |
| Basal Petal Spot Color | Green-Yellow Group 1C. | White Group 157D. |
| Petal Count | Semi-Double 12 to 14. | Double 20 to 25. |

Parents: 'POULor'×'unnamed seedling'.

FLOWER AND FLOWER BUD

Blooming habit: Recurrent to nearly continuous.

Flower bud:

*Size.*—Upon opening, 20 mm–25 mm in length from base of receptacle to end of bud.

*Bud form.*—Elongated, pointed ovoid to high-centered.

*Bud color.*—As sepals unfold, Red Group 52A to Red Group 53C at ¼ opening.

*Sepals.*—Green Group 137A. Weak foliaceous appendages. Surfaces of sepals moderately to slightly pubescent. Stipitate glands present in moderate numbers on exterior surfaces of sepals. Sepals are 30 mm long and 8 to 10 mm wide.

*Receptacle.*—Surface: Smooth, lacking hairs. Shape: Urn-shaped to pear-shaped. Size: Medium, 5 mm–6 mm (h)×5 mm (w). Color: Green Group 146A.

*Peduncle.*—Surface: Variable, some with moderate to numerous stipitate glands. Some lacking glands. Length: 60 mm to 85 mm average length. Color: Yellow-Green Group 146A, with some intonation of Greyed-Red Group 181A. Strength: Somewhat strong.

*Borne.*—Multiple, generally with 5 to 10 buds per flowering stem.

Flower bloom:

*Fragrance.*—Light floral scent.

*Duration.*—As a cut flower 2 to 4 days. The blooms have a duration on the plant of approximately 5 to 7 days. Petals fall cleanly away from plant. Numerous flowers per plant give overall impression of nearly continuous blooming.

*Size.*—Medium. Average flower diameter is 50 mm to 60 mm when open.

*Form.*—Semi-double. Pointed ovoid buds to a flat flower. Shape of flower when viewed from the side: Upon opening, upper part: Flattened convex. Upon opening, lower part: Flattened convex. Open flower, upper part: Flat. Open flower, lower part: Flat.

*Petalage.*—Semi-double. Average range: 12 to 14 petals under normal conditions with 0 to 2 petaloids.

Color:

*Upon opening, petals.*—Outermost petals: Upper Surface: Red Group 53C, with occasional vertical streak of White Group 155C. Reverse Side: Red Group 53D to Red-Purple Group 57A. Innermost petals: Upper Surface: Red Group 43A, with occasional vertical streak of White Group155C. Reverse Side: Red Group 53 D.

*Upon opening, basal petal spots.*—Petals spots: Outer Side: Green-Yellow Group 1C. Inner Side: Green-Yellow Group 1C.

*After opening, petals.*—Outermost petals: Upper Surface: Red Group 53C, with occasional vertical streak of White Group155C. Reverse Side: Red Group 53D to Red-Purple Group 57A. Innermost petals: Upper Surface: Red Group 53C, with occasional vertical streak of White Group 155C. Reverse Side: Red Group 53D.

*Upon opening, basal petal spots.*—Petals spots: Outer Side: Green-Yellow Group 1C. Inner Side: Green-Yellow Group 1C.

General tonality: On open flower, Red Group 53B–D. No change in the general tonality at the end of the $2^{nd}$ day. Afterwards, general tonality is Red Group 53D.

Petals:

*Petal reflex.*—Slight to none.

*Petal edge.*—Edges have point in center of margin.

*Shape.*—Deltoid.

*Petaloids.*—Quantity: 0 to 3. Size: 4 mm (w)×10 mm (l). Color: Red Group 53B–D. Texture: Smooth.

*Thickness.*—Average.

*Arrangement.*—Informal.

*Texture.*—Smooth.

Reproductive organs:

*Pollen.*—Color: Yellow-Orange Group 22A. Abundance: Average.

*Anthers.*—Size: 2 mm long. Color: Yellow Orange Group 22A–22B. Quantity: 30 to 35.

*Filaments.*—Color: Green-Yellow Group 1C. Occasional intonations of Red-Purple Group 68B.

*Stigmas.*—Inferior in position to anthers. Color: Green-Yellow Group 1C.

*Styles.*—Color: Green-White Group 157A. Quantity: 15 to 20. Length: 3 mm. Other: Below stigma there are occasional intonations of Red-Purple Group 68A.

*Hips.*—None observed.

PLANT

Plant growth: Vigorous, compact, upright to bushy. When grown as a budded field grown plant on multiflora understock, the average height of the plant itself is 50 cm to 60 cm and the average width is 50 cm to 60 cm.

Stems:

*Color.*—Young wood: Green Group 143C. Older wood: Green Group 143B.

*Prickles.*—Incidence: Moderate. Size: Average length: 3 mm–5 mm. Color: Yellow-Green Group 144A. As thorns mature, color charges to Greyed-Orange Group174A. Shape: Concave.

*Surface.*—Young wood: Smooth. Older wood: Smooth.

Plant foliage: Normal number of leaflets on leaves in middle of the stem: 7 leaflets.

*Leaf size*.—Medium. 120 mm–150 mm (l)×55 mm–65 mm (w).

*Abundance*.—Above-average abundance.

*Color*.—Upper Leaf Surface: Green Group 137A. Lower Leaf Surface: Green Group 147B. Juvenile foliage: Upper Leaf Surface: Green Group 137A. Lower Leaf Surface: Green Group 147B. Anthocyanin intonation: Location: On young petioles, stipules, thorns, stems, leafrachis, margins and undersides of leaflets. Color: Greyed-Red Group 181A.

Plant leaves and leaflets:

*Stipules*.—Size: Large. 20 mm(l.)–9 mm(w.). Sepals tend to extend entire length of petiole. Extensions are long. Color: Green Group 137A to Yellow-Green Group 146D. Stipitate Glands: Present on margins in average quantities.

*Petiole*.—Length: Range 1 mm–7 mm. Color: Green Group 137A. Underneath: Small prickles present. Margins: Stipitate glands present.

*Rachis*.—Color: Green Group 137A. Underneath: Small prickles present. Margins: Stipitate glands present.

*Leaflet*.—Edge: Finely serrated. Shape: Ovate. Other: Moderately glossy, thick, and leathery. Stipitate glands present on margins and leaflet petioles.

Disease resistance: Above average resistance to mildew, rust, black spot, and Botrytis under normal growing conditions in Jackson County, Oreg.

Cold hardiness: 'POULerry' has been found to be resistant to damage from cold, heat and drought damage in USDA Zone 7.

We claim:

1. A new and distinct variety of rose plant of the shrub class, substantially as herein illustrated and described as a distinct and novel rose variety due to its abundant, red-purple flowers, vigorous and compact growth, strong even growth, low maintenence requirement, and extended period of bloom.

* * * * *

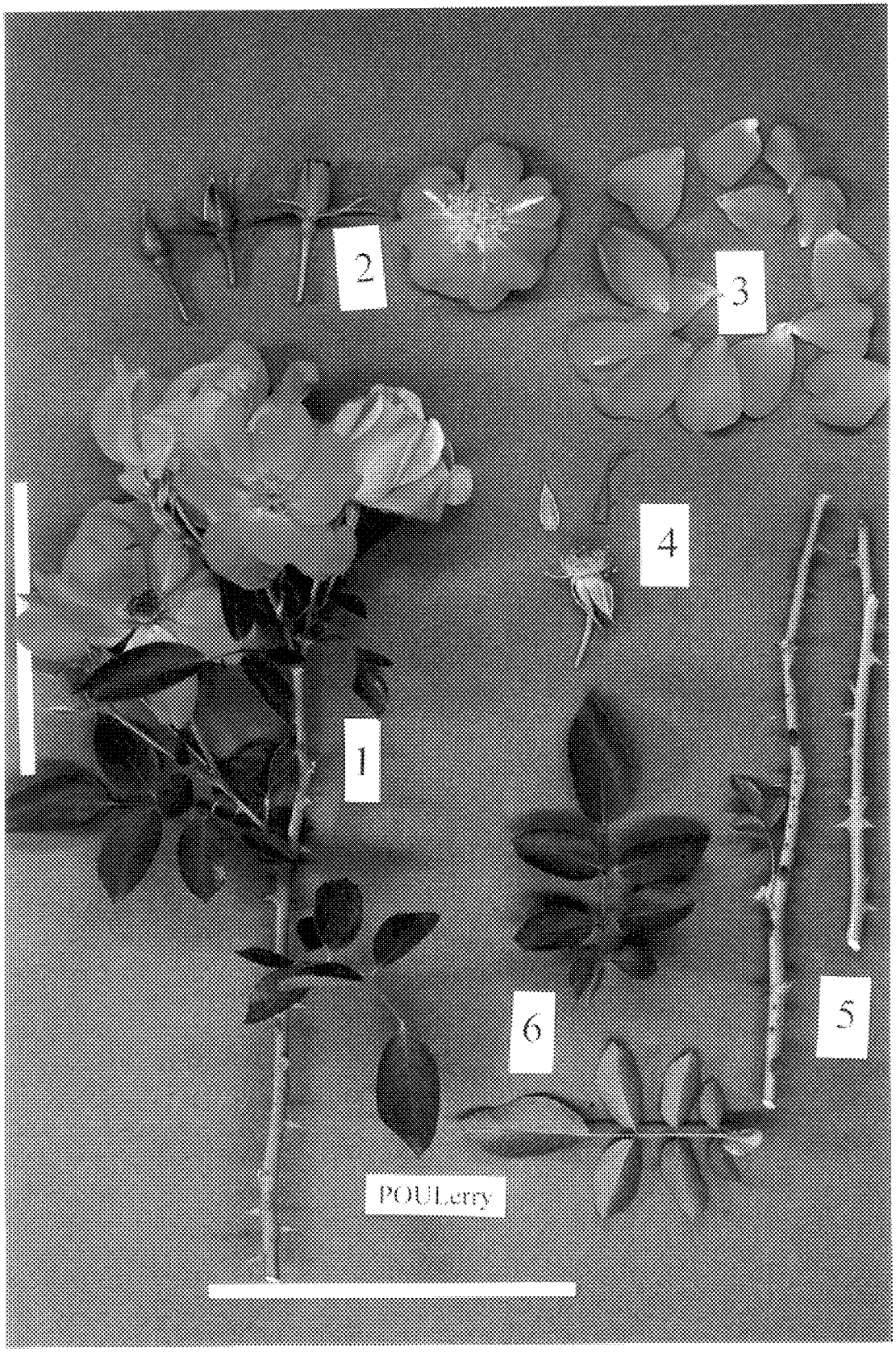
2
3
4
1
6
5
POULerry